(12) United States Patent
Rudin et al.

(10) Patent No.: US 10,079,003 B2
(45) Date of Patent: Sep. 18, 2018

(54) METHOD AND DEVICE FOR IMAGING A REGION OF INTEREST

(75) Inventors: Stephen Rudin, Williamsville, NY (US); Daniel R. Bednarek, Cheektowaga, NY (US)

(73) Assignee: The Research Foundation for the State University of New York, Amherst, NY (US)

( * ) Notice: Subject to any disclaimer, the term of this patent is extended or adjusted under 35 U.S.C. 154(b) by 325 days.

(21) Appl. No.: 14/122,776

(22) PCT Filed: Jun. 4, 2012

(86) PCT No.: PCT/US2012/040803
§ 371 (c)(1),
(2), (4) Date: Feb. 28, 2014

(87) PCT Pub. No.: WO2012/167277
PCT Pub. Date: Dec. 6, 2012

(65) Prior Publication Data
US 2014/0198131 A1    Jul. 17, 2014

Related U.S. Application Data

(60) Provisional application No. 61/492,662, filed on Jun. 2, 2011.

(51) Int. Cl.
| | |
|---|---|
| *G09G 5/00* | (2006.01) |
| *G09G 5/377* | (2006.01) |
| *A61B 6/12* | (2006.01) |
| *A61B 6/00* | (2006.01) |
| *G06T 5/50* | (2006.01) |

(52) U.S. Cl.
CPC ........... *G09G 5/377* (2013.01); *A61B 6/12* (2013.01); *A61B 6/463* (2013.01); *A61B 6/487* (2013.01); *A61B 6/504* (2013.01); *A61B 6/5211* (2013.01); *G06T 5/50* (2013.01); *A61B 6/469* (2013.01); *G06T 2207/10121* (2013.01); *G06T 2207/20221* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 5,467,380 A | 11/1995 | De Jonge et al. | |
| 6,823,086 B1 | 11/2004 | Dolazza | |
| 7,116,752 B2 | 10/2006 | Takahashi et al. | |
| 2005/0084073 A1* | 4/2005 | Seppi | A61B 6/032 378/156 |
| 2006/0062353 A1* | 3/2006 | Yatsenko | A61B 6/032 378/156 |
| 2006/0182224 A1 | 8/2006 | Besson | |
| 2007/0100226 A1* | 5/2007 | Yankelevitz | A61B 5/1075 600/407 |

(Continued)

*Primary Examiner* — Barry Drennan
*Assistant Examiner* — Khoa Vu
(74) *Attorney, Agent, or Firm* — Hodgson Russ LLP

(57) ABSTRACT

Methods and systems of displaying an image of an object are described. The displayed image is comprised of at least two parts that are displayed so as to present a unified image of the object. One part of the image is derived using a first temporal filter and the other part of the image is derived using a second temporal filter.

30 Claims, 22 Drawing Sheets

(56) References Cited

U.S. PATENT DOCUMENTS

| | | | |
|---|---|---|---|
| 2007/0211853 A1* | 9/2007 | Curtis | A61B 6/032 378/53 |
| 2008/0152205 A1* | 6/2008 | Vaillant | A61B 6/032 382/132 |
| 2009/0097723 A1* | 4/2009 | Washburn | A61B 8/06 382/128 |
| 2009/0136112 A1* | 5/2009 | Bismuth | G06T 5/002 382/132 |
| 2010/0034441 A1 | 2/2010 | Makram-Ebeid et al. | |
| 2010/0290693 A1* | 11/2010 | Cohen | A61B 6/469 382/134 |
| 2011/0058723 A1* | 3/2011 | Jandt | G06T 11/005 382/131 |
| 2011/0137156 A1* | 6/2011 | Razzaque | A61B 19/5244 600/424 |
| 2013/0064469 A1* | 3/2013 | Koehler | G06T 5/50 382/261 |

* cited by examiner

METHOD AND DEVICE FOR IMAGING A REGION OF INTEREST

CROSS-REFERENCE TO RELATED APPLICATION

This application claims the benefit of priority to U.S. provisional patent application Ser. No. 61/492,662, filed on Jun. 2, 2011.

FIELD OF THE INVENTION

The present invention relates to methods and devices for imaging a region of interest. The present invention may be embodied as a method of displaying an image of an object (including part of an object) that has been generated using dynamic x-ray imaging, such as that used in a fluoroscopic x-ray system, digital angiography, digital subtraction angiography ("DSA"), cine or in industrial settings where flaws in a manufactured article are to be detected.

BACKGROUND OF THE INVENTION

Dynamic x-ray imaging systems are used for both diagnosis and image-guided procedures in a variety of places, including the human body. For example, x-ray image-guided vascular interventions are carried out by guiding a catheter through the patient's vasculature while a series of images depicting the catheter and the patient's vasculature are displayed to a physician. A primary example of such a procedure used in providing treatment of vascular diseases is a minimally invasive procedure commonly referred to as endovascular image-guided intervention ("EIGI"). EIGIs generally involve the insertion of a catheter into the femoral artery, which is then guided through the patient's vasculature to the site of the pathology to be treated. Fluoroscopic images provided to the physician allow the physician to identify the current position of the catheter tip, as well as how the catheter tip might be guided further through the vasculature. The temporal resolution of existing fluoroscopic systems is quite good, and so the image presented to the physician shows the catheter tip at or very near the actual position of the catheter tip, but the generated images are relatively noisy because of the lower exposure per frame that is often used in an EIGI procedure.

Three images from a longer neurovascular interventional sequence are presented in FIGS. 1, 2 and 3 to provide a better understanding of an EIGI procedure. FIGS. 1, 2 and 3 show different stages of an EIGI procedure conducted to reach an aneurysm. As can be seen from these figures, the acquired images are noisy. Although the image quality may be improved by increasing the radiation per frame, doing so would expose the patient to more radiation for a given procedure. Since images are obtained at a frame rate usually of 7.5 fps to 30 fps during a fluoroscopic procedure, the integral dose to the patient can be substantial. There is a need for a method and system which reduces the integral dose, and yet also reduces the noise in acquired images.

SUMMARY OF THE INVENTION

The invention may be embodied as a method of displaying an image of an object that has been dynamically x-rayed. One such method is depicted in the flow chart found at FIG. 4. In that method, a first image data set ("IDS"), that is representative of the object at a first time, is gathered 10, and a second IDS, that is representative of the object at a second time, is gathered 13. One or both IDSs may include a plurality of pixel data, wherein each pixel data represents radiation received at a specific pixel location on a receiver. For example, one or both of the IDSs may be gathered using a fluoroscopic x-ray system.

A first portion and a second portion of the first IDS are identified 16. The first portion of the first IDS is representative of a first part of the object, and the second portion of the first IDS is representative of a second part of the object. A first portion and a second portion of the second IDS are identified 19. The first portion of the second IDS is representative of the first part of the object, and the second portion of the second IDS is representative of the second part of the object.

A first filter is applied 22 using the first portion of the first IDS and the first portion of the second IDS, in order to produce a first display data set that is representative of the first part of the object. A second filter is applied 25 using the second portion of the first IDS and the second portion of the second IDS, in order to produce a second display data set that is representative of the second part of the object. An image of the object is displayed 28, wherein a first part of the image depicting the first part of the object is displayed using the first display data set, and a second part of the image depicting the second part of the object is displayed using the second display data set.

The first portion of the first IDS and the first portion of the second IDS may be selected to include a catheter tip, or a site that is of interest, such as a treatment site or the site of a flaw in a manufactured article.

The first filter may be a temporal filter that (a) multiplies data of the first IDS by a number $\alpha$ to produce a first output, (b) multiplies data of the second IDS by a number $\beta$ to produce a second output; and (c) adds the first output to the second output to produce the first display data set. The first filter may add the first and second outputs by adding data of the first output that corresponds to data of the second output, wherein data of the first output that corresponds to data of the second output are derived from the same pixel location (i.e. the corresponding output data were derived from the same location on the receiver).

The second filter may be a temporal filter that (a) multiplies data of the first IDS by a number $\psi$, where $\psi$ is different from $\alpha$; to produce a third output, (b) multiplies data of the second IDS by a number $\omega$ to produce a fourth output, and (c) adds the third output to the fourth output to produce the second display data set. The second filter may add the third and fourth outputs by adding data of the third output that corresponds to data of the fourth output, wherein data of the third output that corresponds to data of the fourth output are derived from the same pixel location.

Another type of temporal filter that may be used for the first filter is a recursive filter. Such a filter may (a) derive a first output using data of the first IDS, and multiply the first output by a number $\alpha$, (b) multiply data of the second IDS by a number $\beta$ to produce a second output, and (c) add the first output to the second output to produce the first display data set. $\beta$ may equal $1-\alpha$. The first filter may add the first and second outputs by adding data of the first output that corresponds to data of the second output, wherein data of the first output that corresponds to data of the second output are derived from the same pixel location.

Another type of temporal filter that may be used for the second filter is a recursive filter. Such a filter may (a) derive a third output using data of the first IDS, and multiply the third output by a number $\psi$, (b) multiply data of the second IDS by a number $\omega$ to produce a fourth output, and (c) add the third output to the fourth output to produce the second display data set. ψ may be different from α. It may be the case that ω equals 1−ψ. The second filter may add the third and fourth outputs by adding data of the third output that corresponds to data of the fourth output, wherein data of the third output that corresponds to data of the fourth output are derived from the same pixel location.

The invention may be embodied as a system of displaying an image. One such system is depicted in FIG. 2. Such a system may have a monitor 37 and a microprocessor 40 for carrying out the method described above. The monitor 37 may be instructed by the microprocessor 40 to display an image of an object that has been dynamically x-rayed (x-rayed at different times). The microprocessor 40 may be programmed to gather a first IDS that is representative of an object at a first time, and to identify a first portion of the first IDS and a second portion of the first IDS. The first portion of the first IDS may be representative of a first part of the object, and the second portion of the first IDS may be representative of a second part of the object.

The microprocessor 40 also may be programmed to gather a second IDS that is representative of the object at a second time, and to identify a first portion of the second IDS and a second portion of the second IDS. The first portion of the second IDS may be representative of the first part of the object, and the second portion of the second IDS may be representative of the second part of the object.

The microprocessor 40 also may be programmed to apply a first filter using the first portion of the first IDS and the first portion of the second IDS, in order to produce a first display data set that is representative of the first part of the object. In addition, the microprocessor 40 may be programmed to apply a second filter using the second portion of the first IDS and the second portion of the second IDS, in order to produce a second display data set that is representative of the second part of the object. The filters may be temporal filters, such as those described above.

The monitor 37 may receive signals from the microprocessor in order to cause the monitor to display an image of the object. A first part of the displayed image depicts the first part of the object using the first display data set, and a second part of the image depicts the second part of the object using the second display data set. In this manner, the displayed image is derived from at least two different data sets obtained at different times. The first and second parts of the displayed image are combined to provide the user with an integrated image of the object. As such, the displayed image may be thought of as a unified image of the object comprising at least two parts.

Providing the data sets to the microprocessor 40 may be a receiver 43 that pixelates the received radiation in the form of electronic signals that are sent to the microprocessor. As such, the IDSs may be a plurality of pixel data, wherein each pixel data represents radiation received at a specific location on the receiver 43. An example of a receiver 43 that may be suitable for this purpose is an image intensifier, such as those commonly found on a fluoroscopic x-ray system.

BRIEF DESCRIPTION OF THE DRAWINGS

For a fuller understanding of the nature and objects of the invention, reference should be made to the accompanying drawings and the subsequent description. Briefly, the drawings are:

In FIG. 22a, a Tracker 18 catheter enters the aneurysm; (22b) there is inadequate clearance between the catheter tip and the aneurysm dome to allow delivery of a 7 mm×30-cm GDC; (22c) the catheter is repositioned to increase clearance; (22d) the coil is advanced out of the microcatheter and begins to assume the natural helical shape in the aneurysm; (22e) the coil is advanced further; (22f) the GDC herniates out of the aneurysm cavity into the lumen of the supraclinoid segment of the carotid artery; (22g) repositioning of the GDC is attempted after removal and redelivery; (22h) the 7 mm×30-cm coil begins to herniate out of the aneurysm cavity again; (22i) an 8 mm×30-cm coil is introduced into the aneurysm; (22j) before completion of a 360 degree turn, the distal end of the coil herniates into the supraclinoid segment of the carotid artery; (22k) after deployment, the 8 mm×30-cm coil assumes an irregular shape and herniates into the carotid artery lumen (arrow); (22l) the 8 mm×30-cm coil begins to curl within the carotid artery outside the aneurysm (arrow); (22m) redeployment of the 8 mm×30-cm coil is still unsuccessful; (22n) digital subtraction angiogram (lateral view) obtained with left internal carotid artery injection shows the coil extending into the carotid artery lumen from the aneurysm cavity.

FURTHER DESCRIPTION OF THE INVENTION

Figure 1:
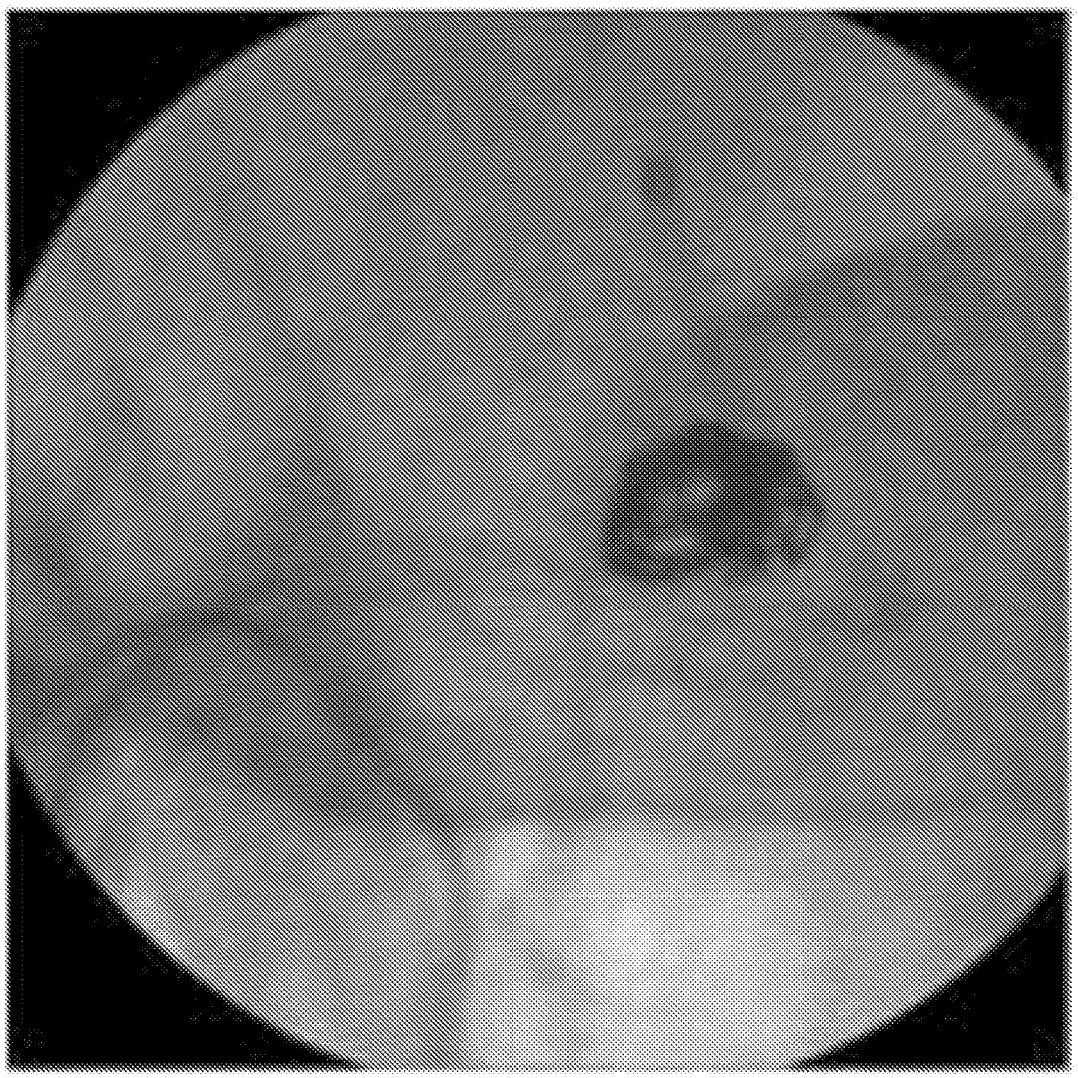
FIG. 1 depicts an image provided by a fluoroscopic system. The image shows a coil wire outside an aneurysm.

Further description of the invention is provided below by describing a GPU based implementation in which computer implemented temporal filters are used to produce an integrated image of an object on a monitor. A temporal filter uses data about an object that is gathered 10, 13 at at least two different times to produce display data sets that can be used to display an image 28 of the object. Each temporal filter may have a different weight associated with it. By applying different filter weights to the temporal filters, one region of the displayed image may achieve a desired image quality that is different from another region of the displayed image. Such an implementation of the invention allows for real-time noise reduction during an endovascular image-guided intervention, and may allow for reduced radiation delivered to some areas of the object being imaged.

At the outset, it should be noted that it is possible to use a radiation attenuator along with the temporal filters, as part of an effort to reduce the radiation received by the object that is being imaged. However, the invention is not limited to use with an attenuator. The attenuator may be placed over a periphery of the area to be imaged, and doing so can substantially reduce the amount of radiation received by the object in the "shadow" of the attenuator, and the temporal filter can help reduce noise in the displayed image that would otherwise arise from use of the attenuator. If the attenuator is sized to correspond with the ROI, then the weight of a temporal filter corresponding to the attenuated region can be increased in order to effectively reduce noise in the resulting displayed image of that region.

For the purpose of describing the invention, we describe a dynamic x-ray system in which an object is fluoroscopically irradiated. By way of example we will discuss the invention with reference to a neurovascular procedure, but the invention is not limited to such a procedure. For example, the invention can be used in other procedures where fluoroscopy-type imaging is used, such as guidance or diagnosis in cardiology (for example valve placements), gastroenterology (such as barium enemas), or other medical procedures as well as non-medical procedures, such as non-destructive imaging of objects (such as machined parts).

A system according to the invention may be implemented using a computer arranged according to CUDA (Compute Unified Device Architecture) by NVIDIA (Santa Clara, Calif.). Best results may be obtained when the computer is able to engage in massive parallel computing, thus achieving a reduction in perceived processing time. The invention should be implemented so that data is processed in a short amount of time so that frame loss is minimized or eliminated, and so that temporal delay experienced via the displayed image is minimized.

We first explain the use of a GPU-implemented rapid temporal filtering technique during an endovascular image guided intervention with normal fluoroscopy. Next we describe its use in combination with ROI fluoroscopy where the exposure is substantially reduced in the peripheral region outside the ROI by an attenuator, and the displayed image is enhanced in brightness and filtered using at least two temporal filters, each being applied to different sets of image data obtained from the fluoroscopy via a fluoroscopic receiver.

In a method according to the invention, an object is irradiated in order to generate and gather 10, 13 a series of images taken over time. That portion of the object that is irradiated includes an ROI and a peripheral region, which together constitute the FOV. The ROI includes the location of something that is of interest, such as an aneurysm, as well as the area close to the aneurysm. The periphery region includes the portion of the irradiated area that is not in the ROI. In some embodiments of the invention, the size of the ROI may be adjusted in order to suit the desires of the user, who may be a physician.

A Micro-Angiography (MAF) x-ray detector [3] may be used to capture 10, 13 image data and store that data on a computer hard disk memory. For example, a first image data set of 1024×1024 pixels with 16 bits in each pixel may be gathered 10 at a first time. The first image data set may be stored on the computer hard drive. A second image data set of 1024×1024 pixels with 16 bits in each pixel may be gathered at 13 a second time The second image data set may be stored on the computer hard drive. Then a microprocessor may be used to implement 22, 25 a temporal filter in a pixel-by-pixel manner in order to produce a display data set that may be used to display an image to the user via a monitor.

The temporal filter may be implemented using software that has been written to effect a recursive filter, such as the following linear recursive filter, with respect to the image data sets that have been generated by the fluoroscopic system:

$$y(t)=\alpha*y(t-1)+(1-\alpha)*x(t) \qquad (1)$$

where x(t) is the current input signal at time "t" (e.g. at the frame number t), y(t−1) is a prior output signal, which may be the immediately previous output signal, y(t) is the present output signal of the filter, and α is the filter weight, which may be referenced as "lag" or "memory".

For clarity, the current input signal may be the value of the data in the second image data set that corresponds to the pixel at column X and row Y that was gathered at the second time, and the prior output signal may be the output of the filter derived for the pixel at column X and row Y when the first image data set was the current input signal. As such, the output of the filter is the weighted sum of its present input and one or more prior outputs. The higher the weight, the greater are the lag and the degree of data smoothing.

By using a temporal filter for noise reduction, there is a reduction in temporal resolution. That is to say that in generating an image that is based on a current image data set as well as one or more prior image data sets, the image that is displayed to the user may not reflect the current status of the object. Instead, the image that is displayed to the user is a combination of images over time.

Another type of temporal filter that might be employed uses the current image data sets and one or more prior image data sets, rather than prior outputs of the filter. Such a temporal filter can be represented by the following equation:

$$y(t)=[\Sigma x(t-p)+x(t)]\div n \qquad \text{(equation 2)}$$

where x(t) is the current input signal at time "t" (e.g. at the frame number t), Σx(t−p) is the sum of one or more prior input signals, y(t) is the present output signal of the filter, and n is the number of input signals (i.e. the number of prior input signals plus 1).

By adjusting the number of prior image data sets (i.e. "p") used in this temporal filter, the temporal resolution may be adjusted to suit the user's needs. Furthermore, the prior input signals may be weighted different from the current input signal in order to suit the user's needs. For example, the temporal filter might be represented by the following equation:

$$y(t)=\alpha*\Sigma x(t-p)+\beta*x(t) \qquad \text{(equation 3)}$$

where

α is the weight given to the prior input signals,

β is the weight given to the current input signal, x(t) is the current input signal at time "t" (e.g. at the frame number t), Σx(t−p) is the sum of one or more prior input signals, and y(t) is the present output signal of the filter.

For example, α may be 0.3 and β may be 0.7. Normally, the sum of α and β is one.

Alternatively, each x(t−p) may have a different weight. For example, as the value of "p" grows, the weight may be reduced so that more recent input signals are given greater weight. By adjusting the weights, the temporal resolution may be adjusted to suit the user's needs. For example, if the weights are selected so that the current input signal and/or very recent input signals have a relatively high cumulative weight relative to older input signals, then the displayed image will exhibit a more temporally accurate representation of the current situation in the object being imaged.

It should be noted that the invention may be implemented to allow the user to change the weights of the temporal filter as the procedure progresses. Also, the number of prior image data sets ("p") may be altered as the procedure progresses. As such, the user can change the image characteristics to accommodate changed conditions arising during the procedure.

Another type of temporal filter may combine features identified above. For example, the current input may be weighted and added to (a) the most recent output y(t−1) weighted with a desired weight, and (b) a sum of weighted prior inputs x(t−p). Such a filter may be described as:

$$y(t)=\alpha(t)*x(t)+\Sigma\alpha(p)*x(t-p)+\beta*y(t-1) \qquad \text{(equation 4)}$$

where α(t) is the weight of the current input, α(p) is the weight for the pth prior input, and β is the weight for the prior output. It may be beneficial to force α(t)+Σα(p)+β=1. By adjusting the number of prior image data sets (i.e. "p") used in this temporal filter, the temporal resolution may be adjusted to suit the user's needs.

Figure 6:
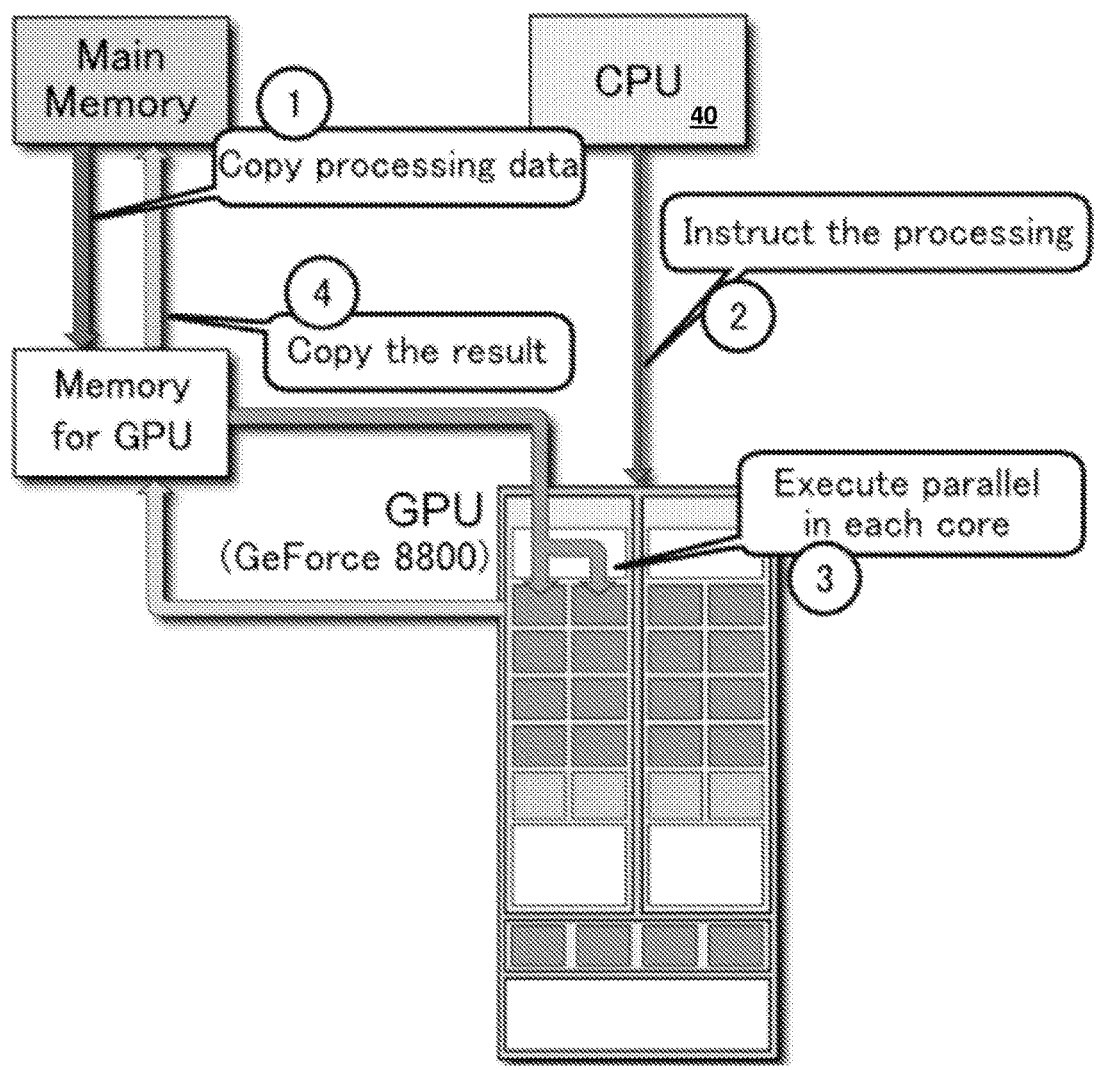
FIG. 6 is a schematic showing a fluoroscopic system that may be used with the present invention.
Figure 7:
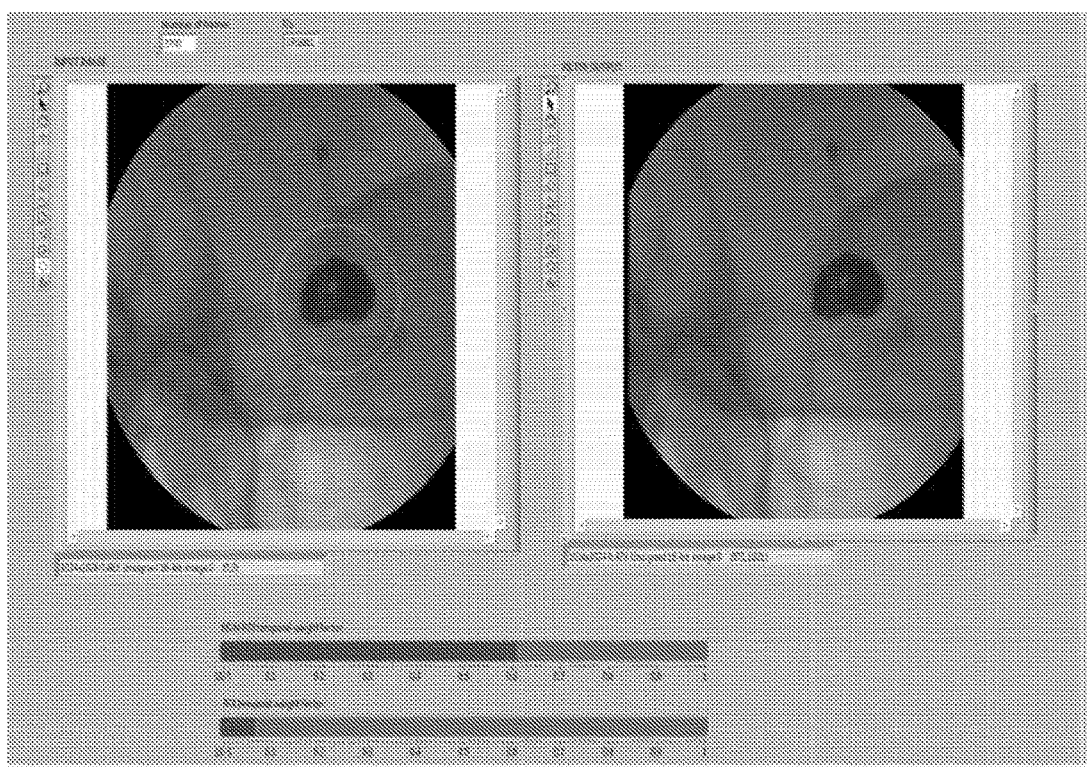
FIG. 7 depicts a monitor displaying two images. The image on the left has not had temporal filtering done to the image data set. The image on the right was generated using a temporal filter according to the invention, and in particular the temporal filters were in keeping with equation (1) below. The upper bar graph indicates the weight used in the periphery, and the lower bar graph indicates the weight used in the ROI. The weight used in the temporal filter was lower in the ROI. Note that the periphery (outside the ROI) of the image on the right is less noisy than the periphery of the image on the left. Although single images are shown in FIG. 7, the user will perceive the rapid substitution of images on the monitor as a video.

Furthermore, rapidly processing the image data sets using a temporal filter will offset at least some of the reduction in temporal resolution arising from use of the temporal filter. The CUDA architecture in combination with the NVIDIA graphics processing unit (GPU) may be used to implement the invention because it is capable of rapidly processing large data sets. FIG. 6 graphically describes in simple terms, a CUDA processing flow. In such a system, it is possible to process the image data sets at a rate of 20 fps ("frame per second", where a frame corresponds to an image data set). A screen shot from the display monitor is presented in FIG. 7.

Figure 8:
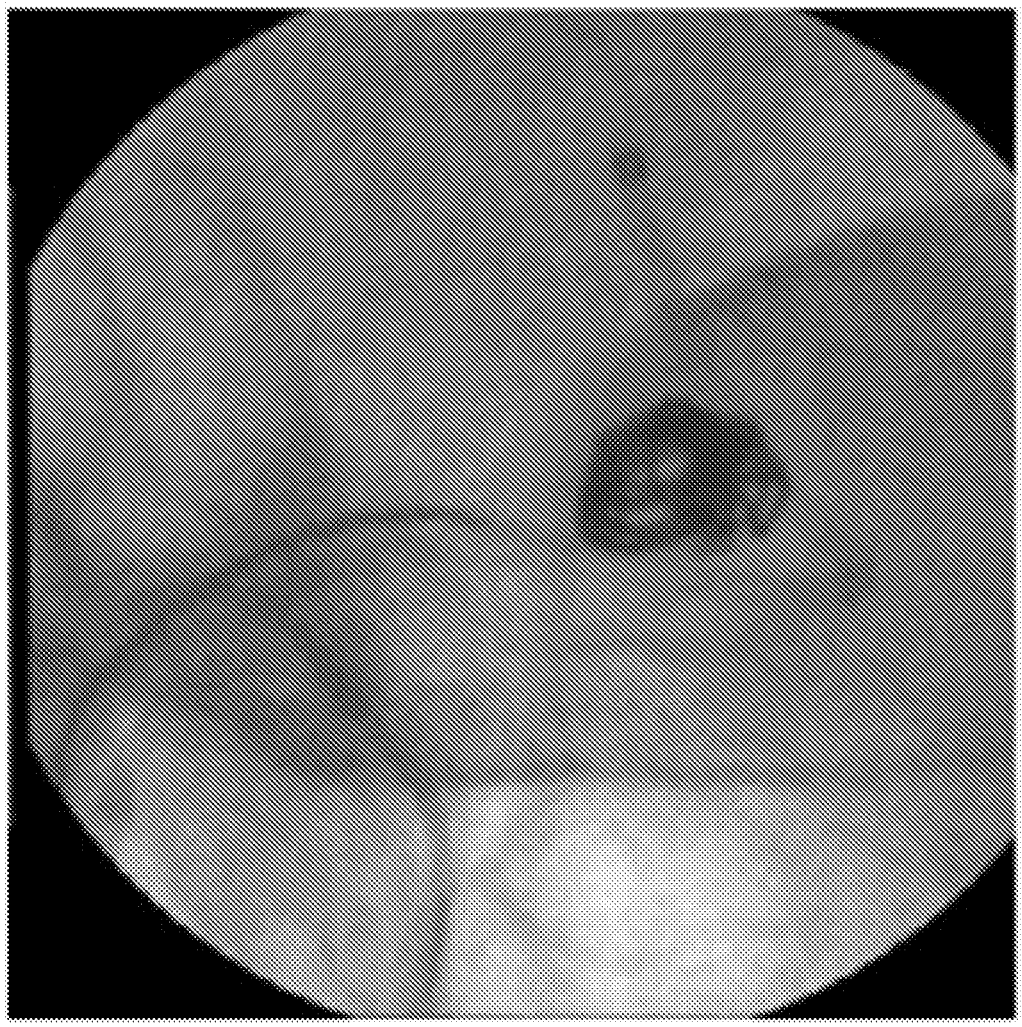
FIG. 8 depicts another image generated and displayed according to the invention in which a temporal recursive filter ("TRF") was used, and the weight in the ROI was 0.70, while the TRF weight outside the ROI was 0.25.
Figure 9:
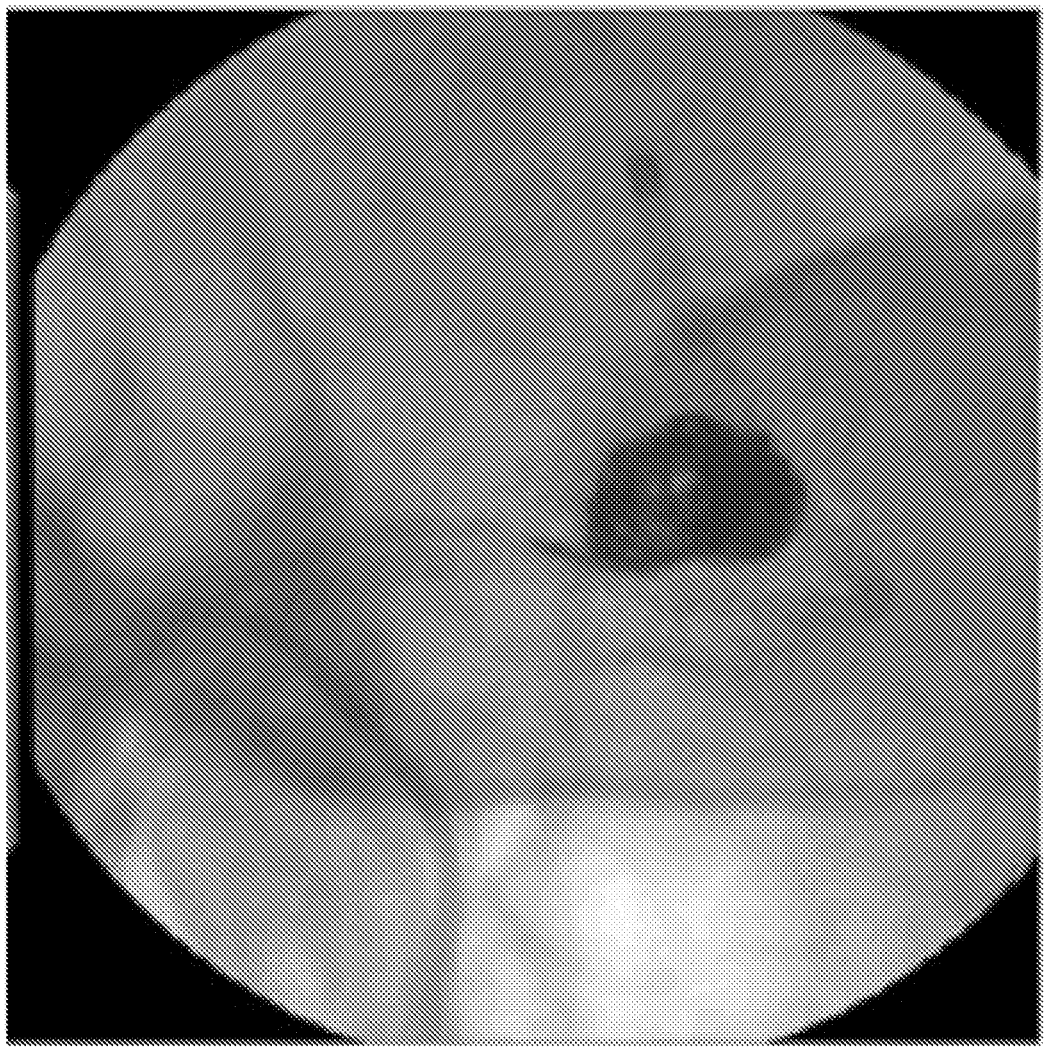
FIG. 9 depicts another image generated and displayed according to the invention in which the TRF weight in the ROI is 0.25, while the TRF weight outside the ROI is 0.7.
Figure 10:
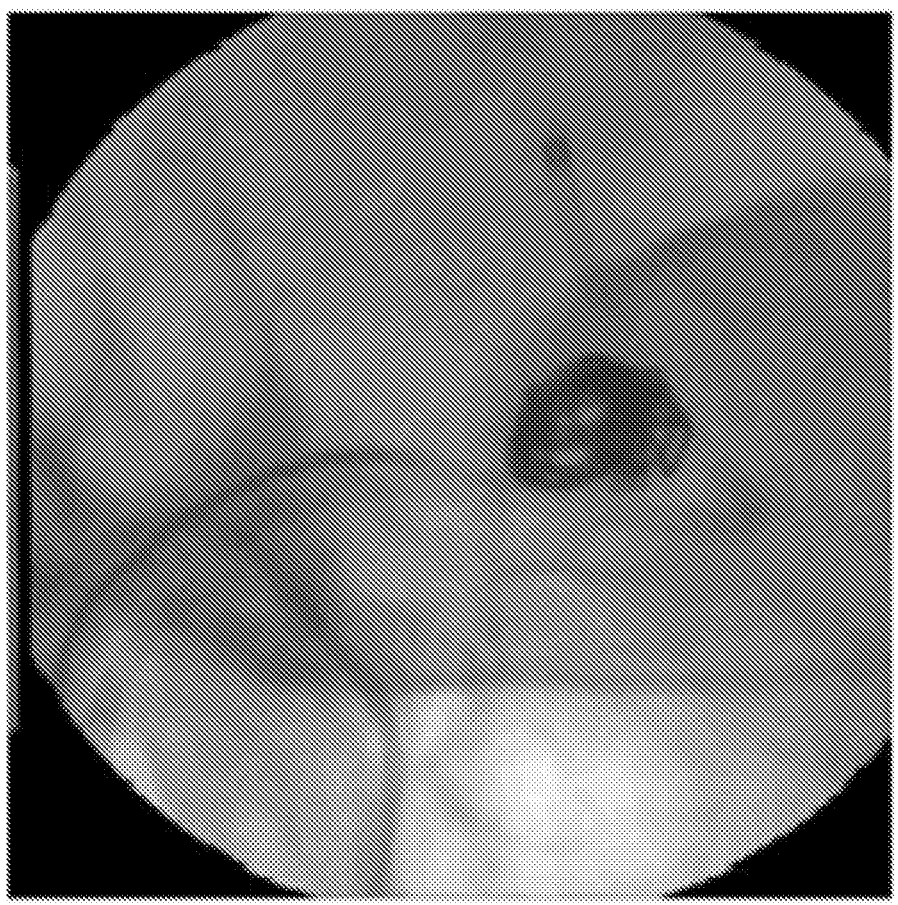
FIG. 10 depicts another image generated and displayed according to the invention in which the TRF weight in the ROI and the TRF weight outside the ROI are both 0.7.

Having described some of the basic features of the invention, the following description provides additional description of the invention as it might be applied to an EIGI under normal fluoroscopy. A circular region around an aneurysm (FIG. 1) of the patient may be selected as the ROI. During the beginning of the intervention, using the presently disclosed technology, while the coil-wire is being guided towards the aneurysm, a lower weight may be selected for the region outside the ROI, to avoid a significant loss in temporal resolution (FIG. 8). Once the tip of the coil-wire is inside the ROI, the weight in the non-ROI or periphery region is increased to reduce noise, thus providing a smoother image to the neurointerventionalist, while the weight in the ROI is decreased to allow unblurred imaging of fine wire and coil movements within the aneurysm itself (FIG. 9). If needed, the weight selected for the temporal filter in the ROI and the weight selected for the temporal filter outside the ROI can be made equal in order to achieve a more uniform image quality. FIG. 10 shows such an image generated by selecting the same weight for a TRF used for the ROI and a TRF used for the region outside the ROI.

When an attenuating filter is used to reduce the radiation received outside the ROI by the patient, noise generally reduces the image quality, and the image is darker due to fewer photons reaching the receiver. The image quality in the ROI is quite different, and is normally brighter and relatively less noisy due to higher exposure. The invention may be used to reduce the noise in the periphery region (outside the ROI), and thereby provide the physician with a more uniform image of the entire FOV (ROI and periphery region). When coupled with known techniques for brightness and contrast restoration, the multiple temporal filtering technique of the present invention can be used to reduce the noise and provide a better quality image sequence, which in turn will assist the user in conducting the procedure.

Figure 2:
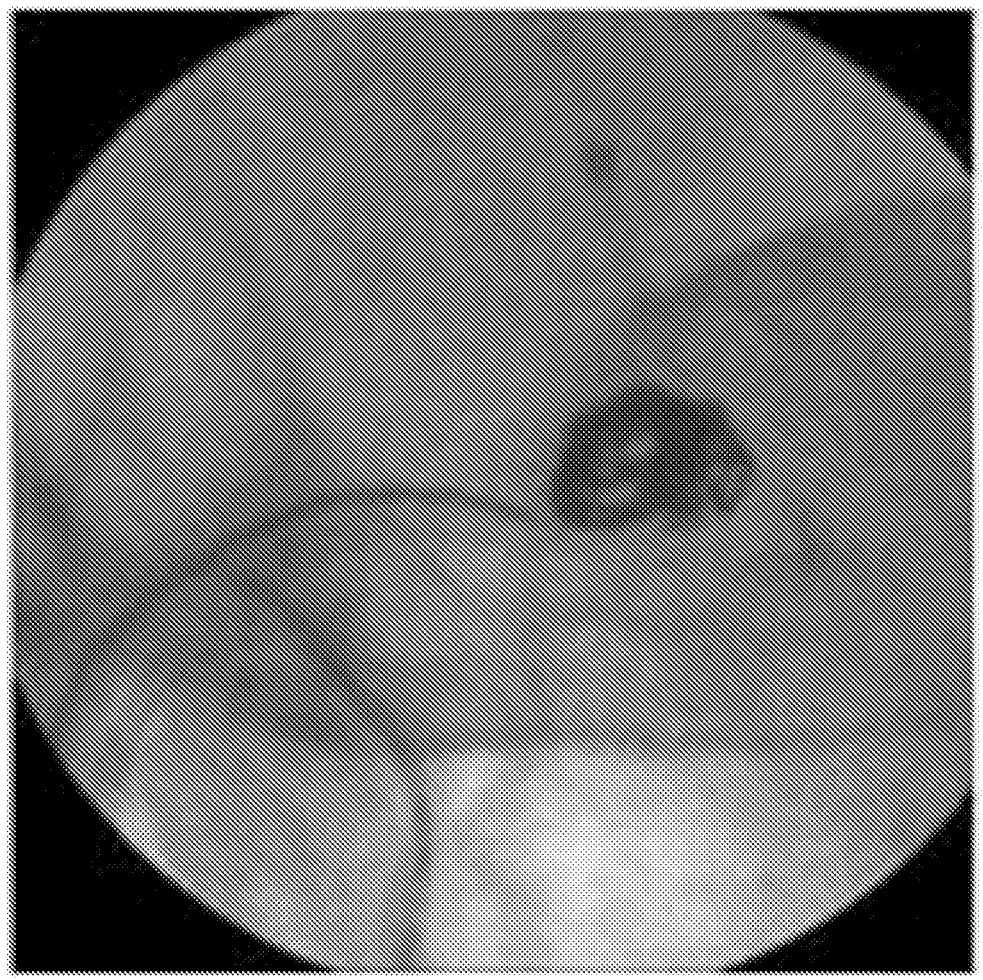
FIG. 2 depicts another image provided by the fluoroscopic system corresponding to FIG. 1. The image shows the coil-wire entering the aneurysm.
Figure 3:
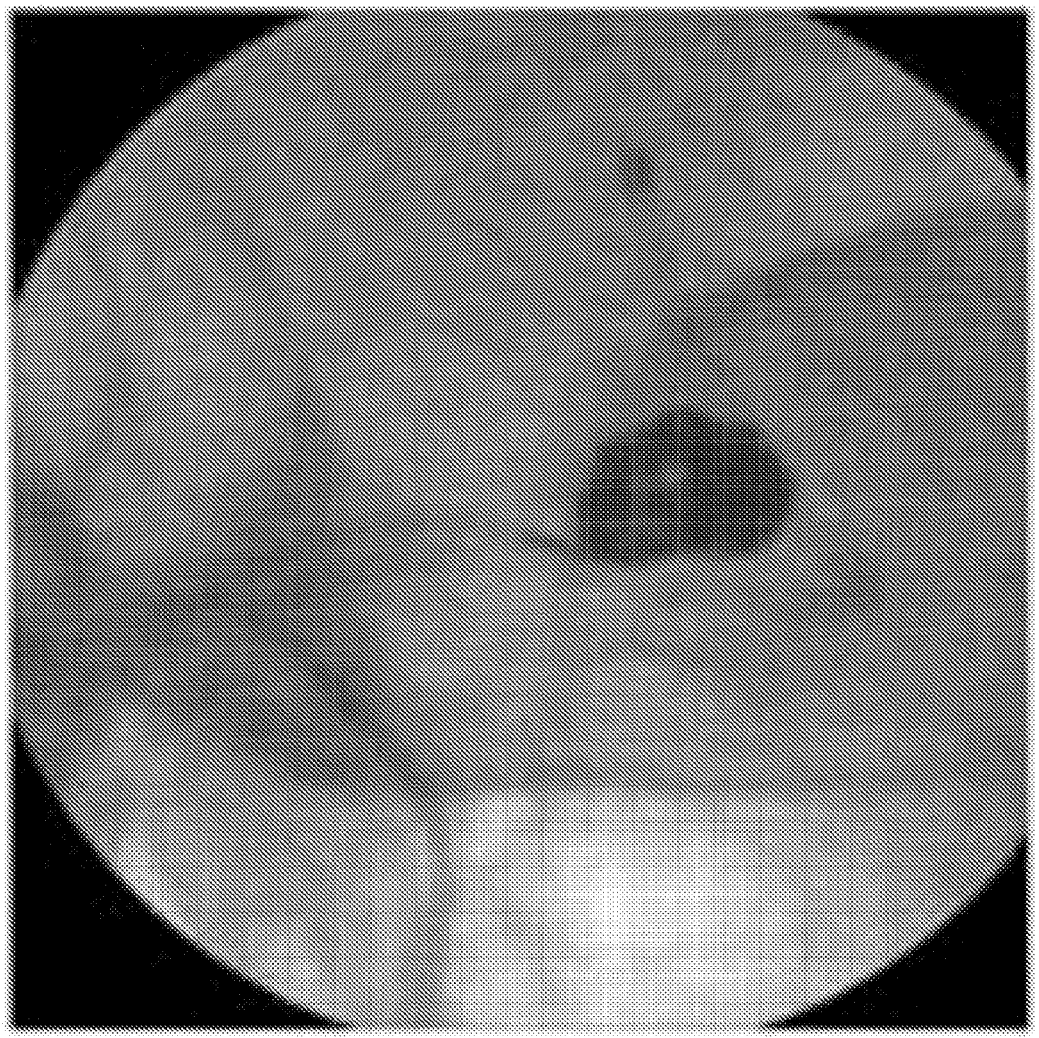
FIG. 3 depicts another image provided by the fluoroscopic system corresponding to FIG. 1. The image shows the coil-wire successfully guided into the aneurysm.
Figure 4:
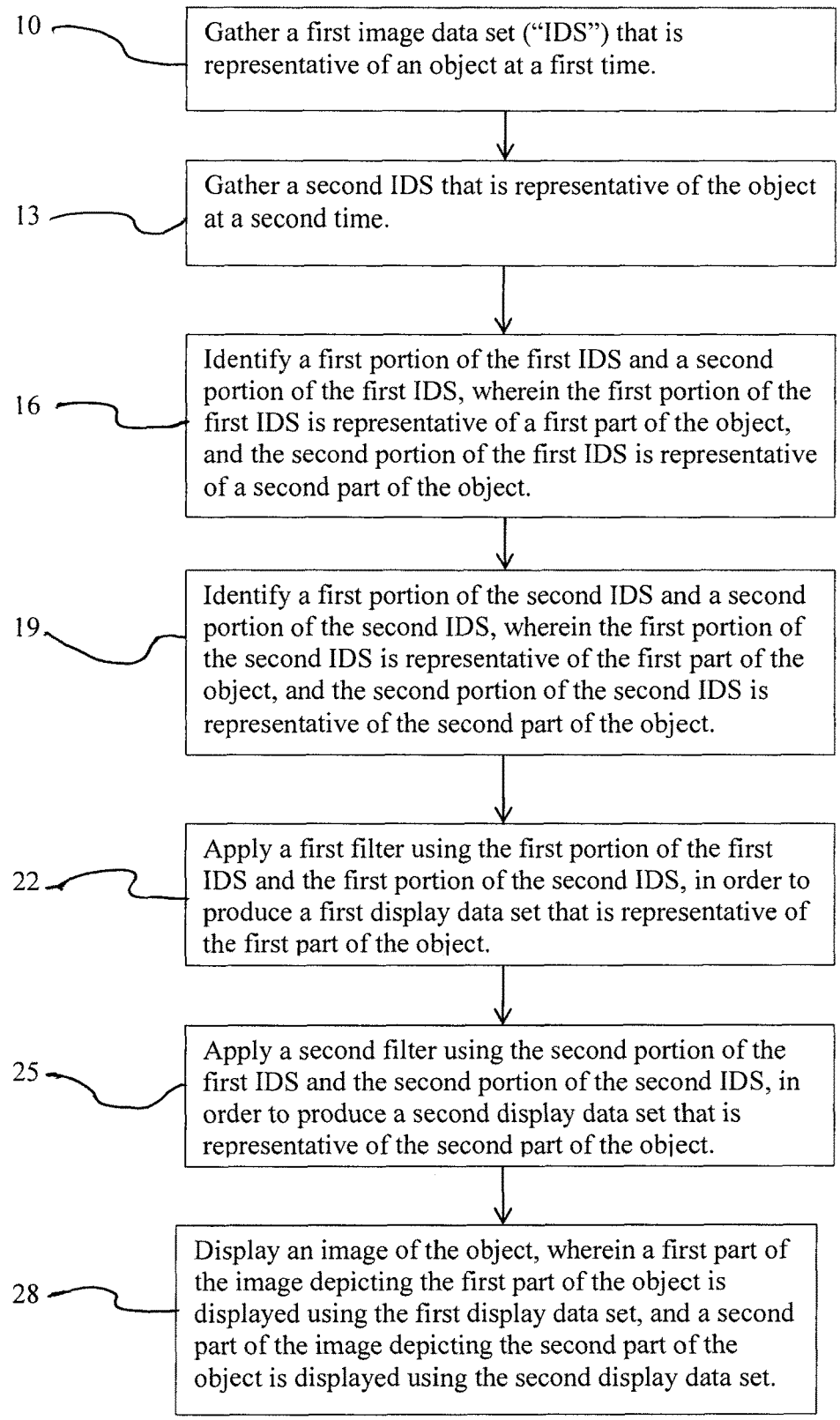
FIG. 4 is a flow chart depicting a method according to the invention.
Figure 5:
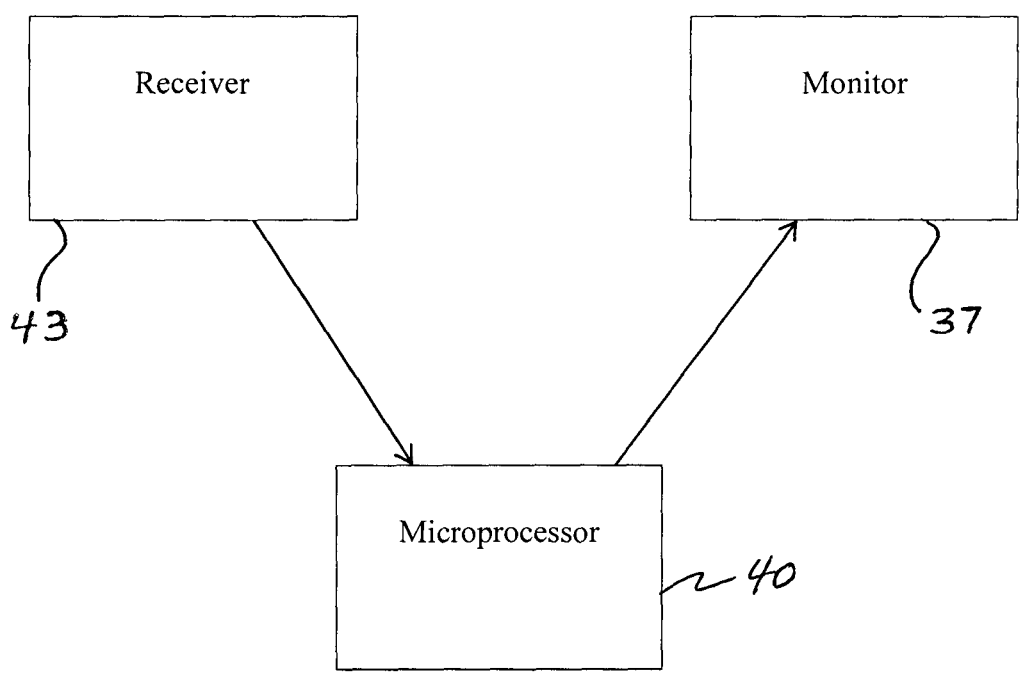
FIG. 5 is a schematic depicting a system according to the invention.
Figure 11:
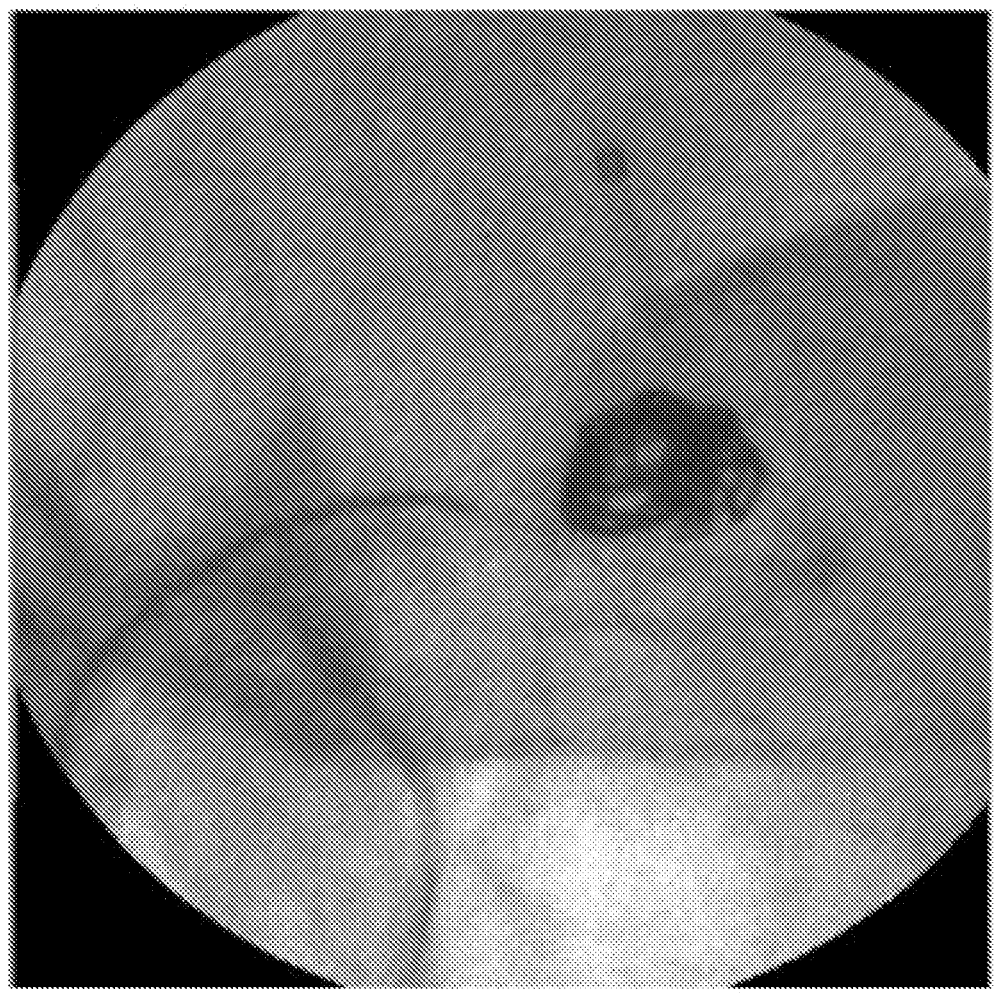
FIG. 11 depicts a fluoroscopically generated image that has been reduced in overall pixel values (dose) by a factor of 10 with Poisson noise added, and the image has been contrast adjusted for reader convenience.
Figure 12:
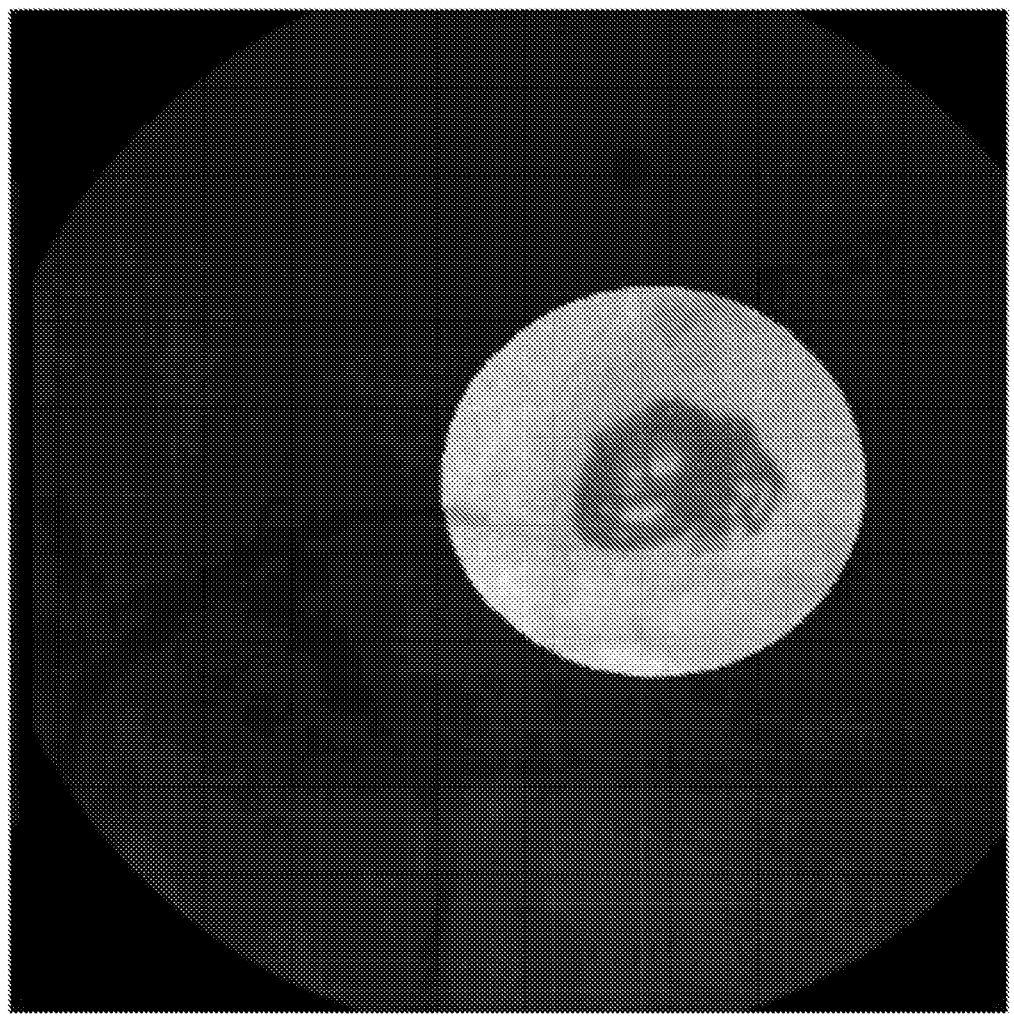
FIG. 12 depicts a fluoroscopically generated image in which the peripheral region has pixel values (dose) reduced by a factor of 10 by using an attenuator.
Figure 13:
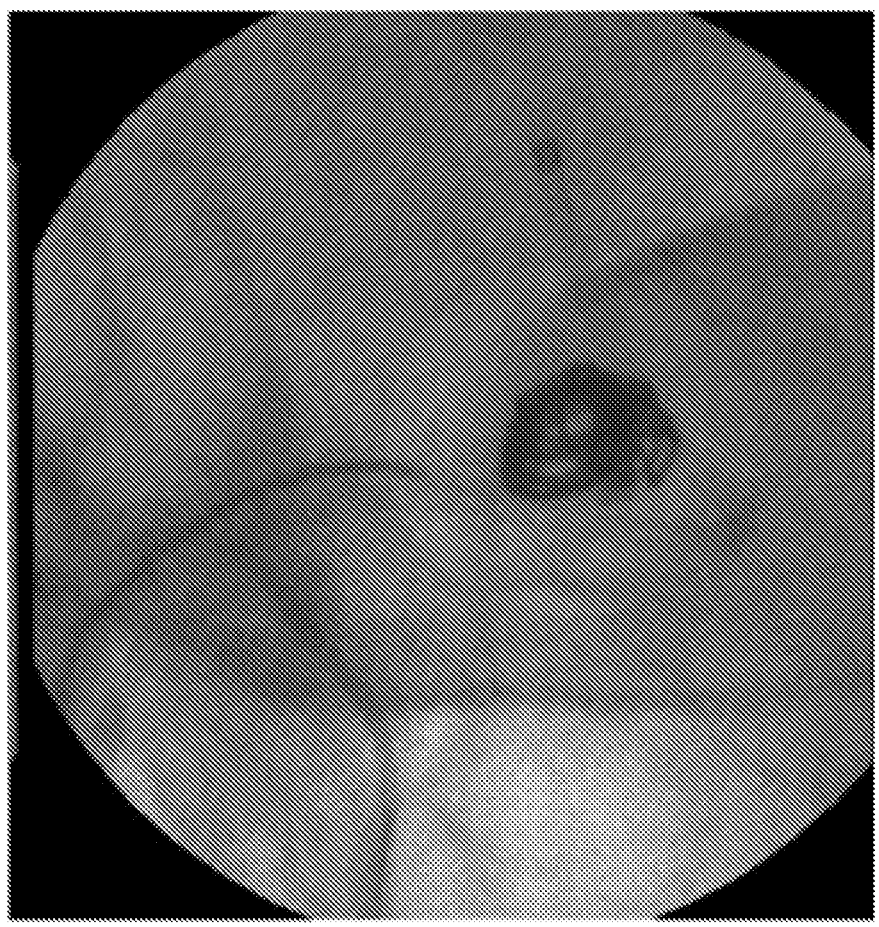
FIG. 13 depicts the image of FIG. 12, but the display brightness has been enhanced outside the ROI.
Figure 14:
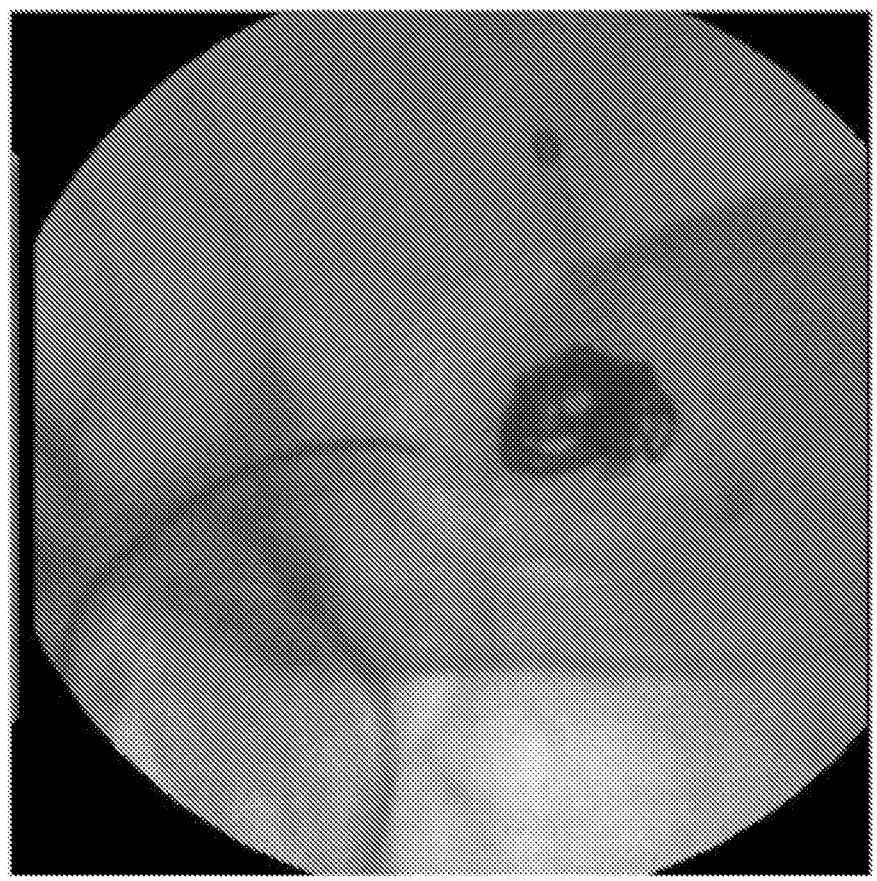
FIG. 14 depicts the image of FIG. 13, but the image is generated and displayed according to the invention in which the TRF weight outside the ROI is 0.75, and the TRF weight in the ROI is zero to reduce the noise appearing as a result of the 10× dose reduction.
Figure 15:
FIG. 15 is a fluoroscopically generated image of a skull phantom obtained with an attenuator in place. The attenuator was a 4-layer kodak lanex material, and the fluoroscopy was run at 80 kvp and tube current 32 ma.
Figure 16:
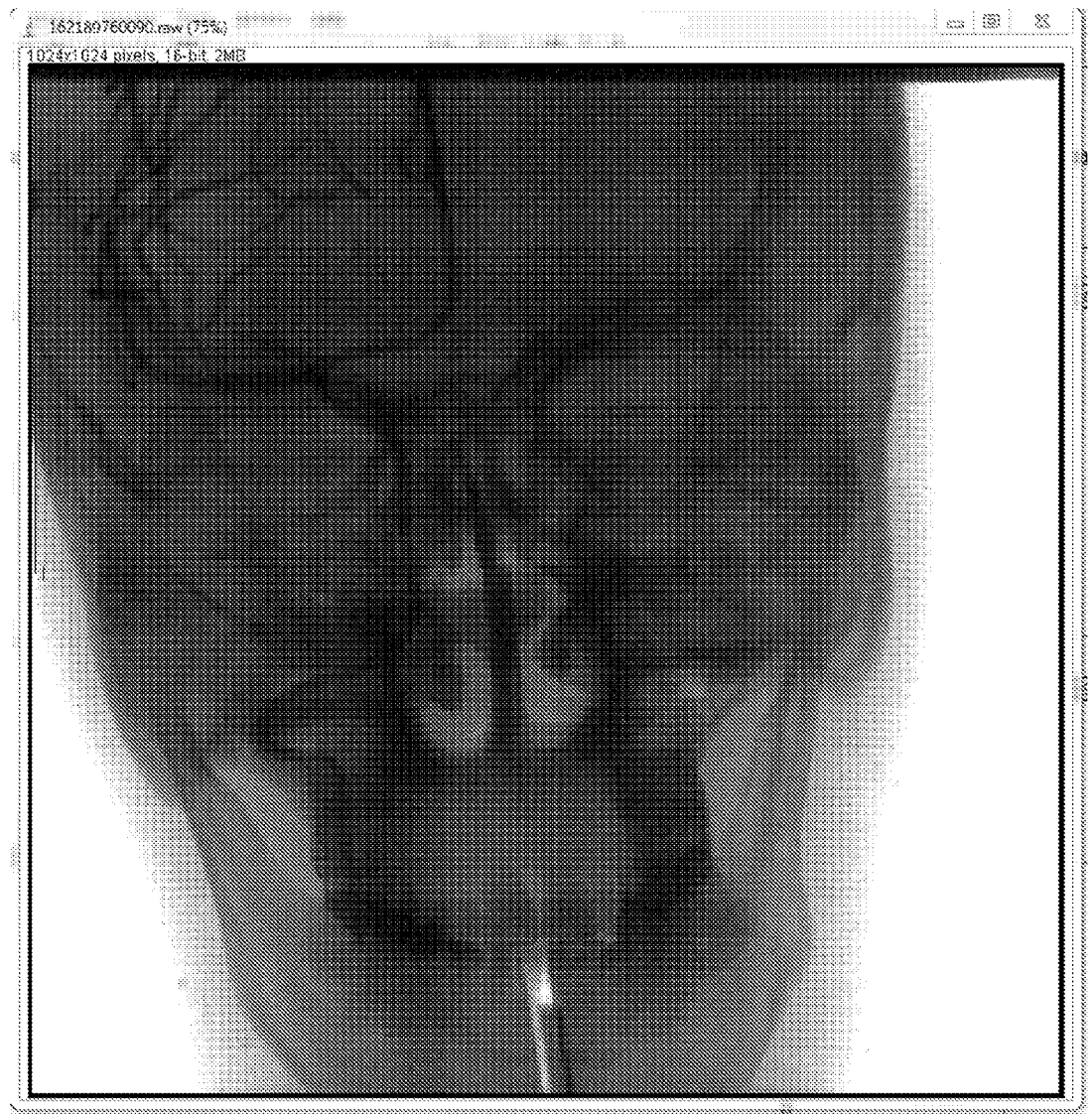
FIG. 16 depicts the skull phantom of FIG. 15 without an attenuator in place.
Figure 17:
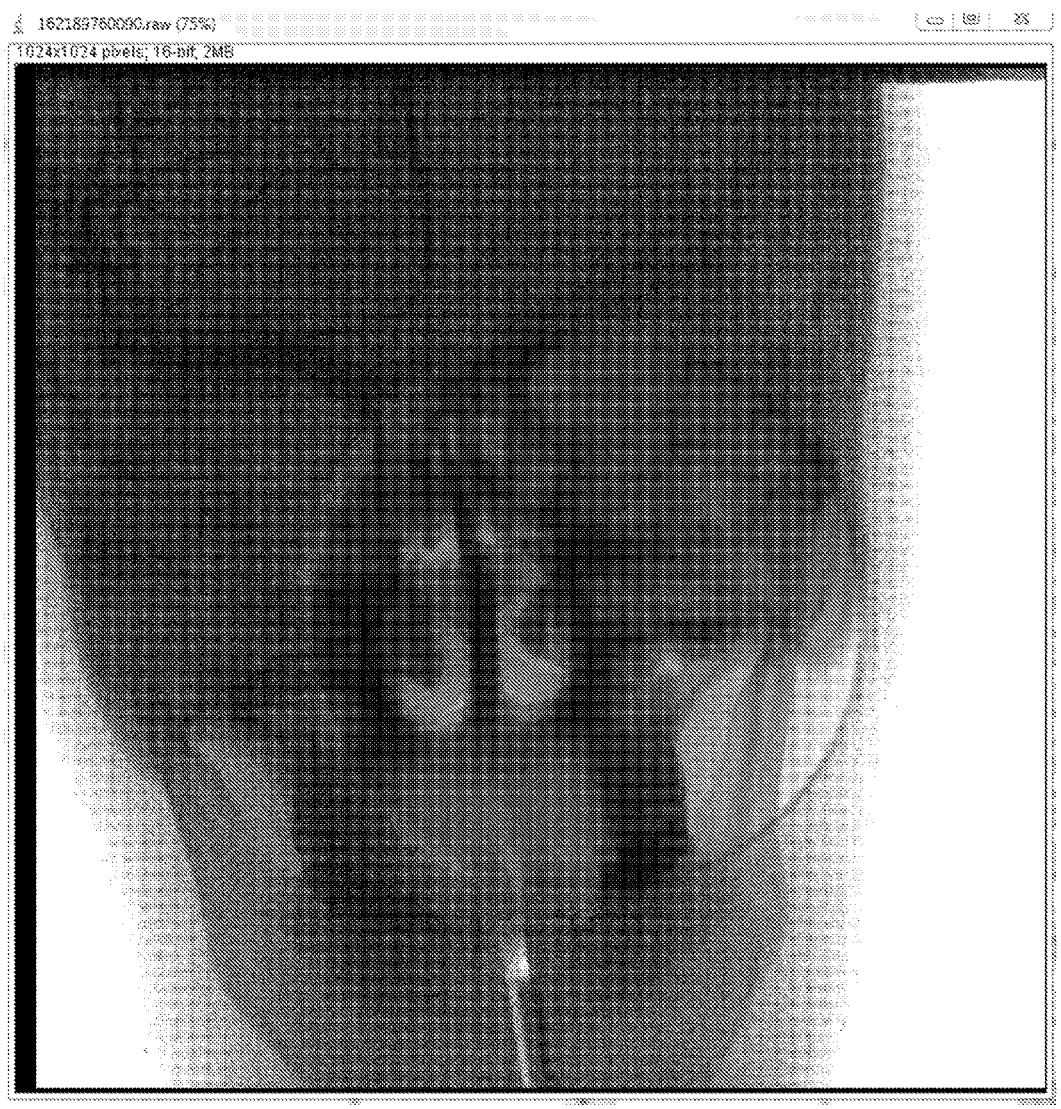
FIG. 17 depicts the skull phantom with the attenuator in place, but the image has been enhanced in brightness outside the ROI. Note the noise in the region outside the ROI.
Figure 18:
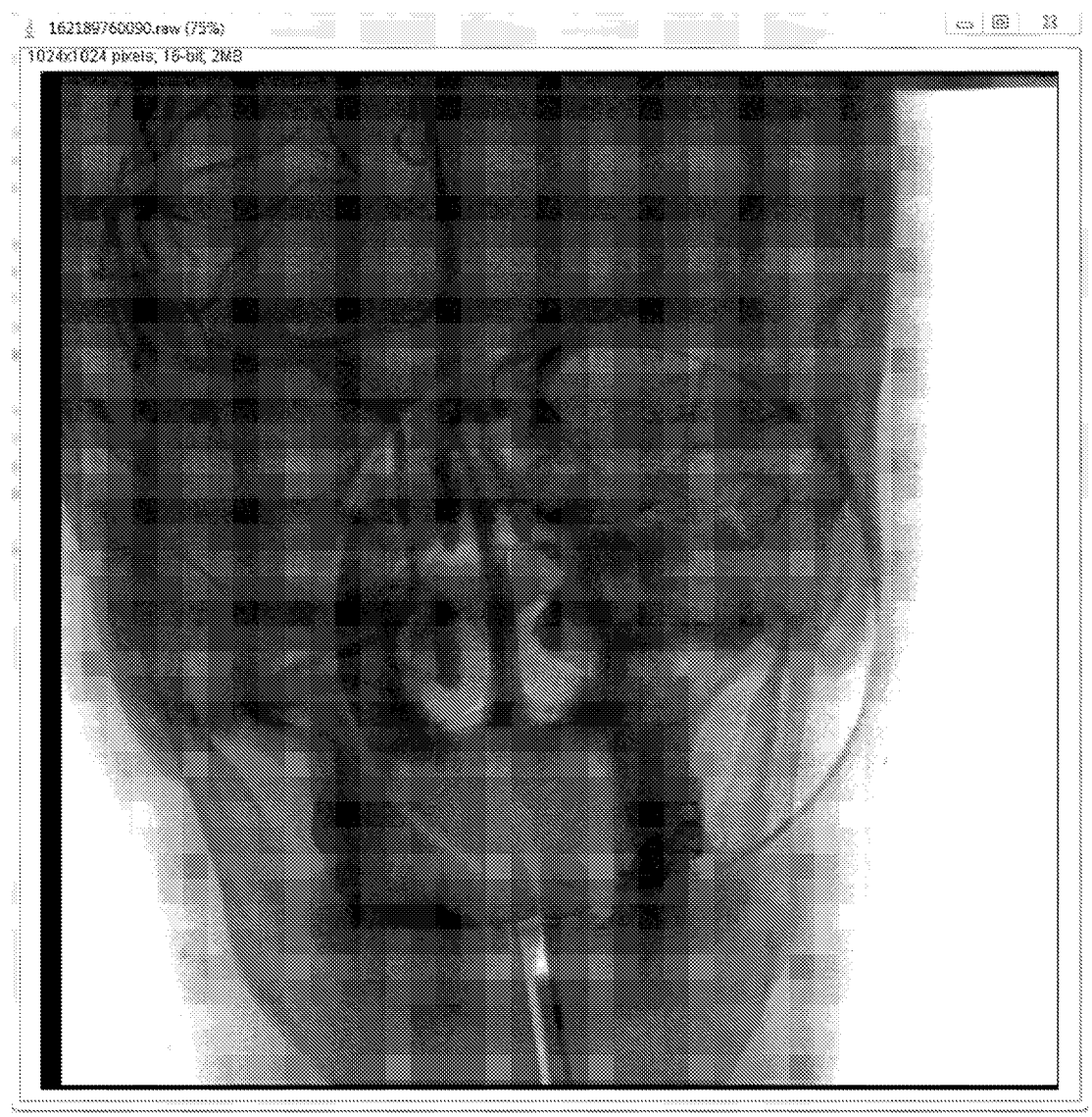
FIG. 18 is an image displayed and generated according to the invention in which the image data sets corresponding to FIG. 17 have been acted upon by a TRF having a weight of 0.8 outside the ROI and a TRF having a weight of zero inside the ROI. Note the reduction in noise compared to FIG. 17.
Figure 19:
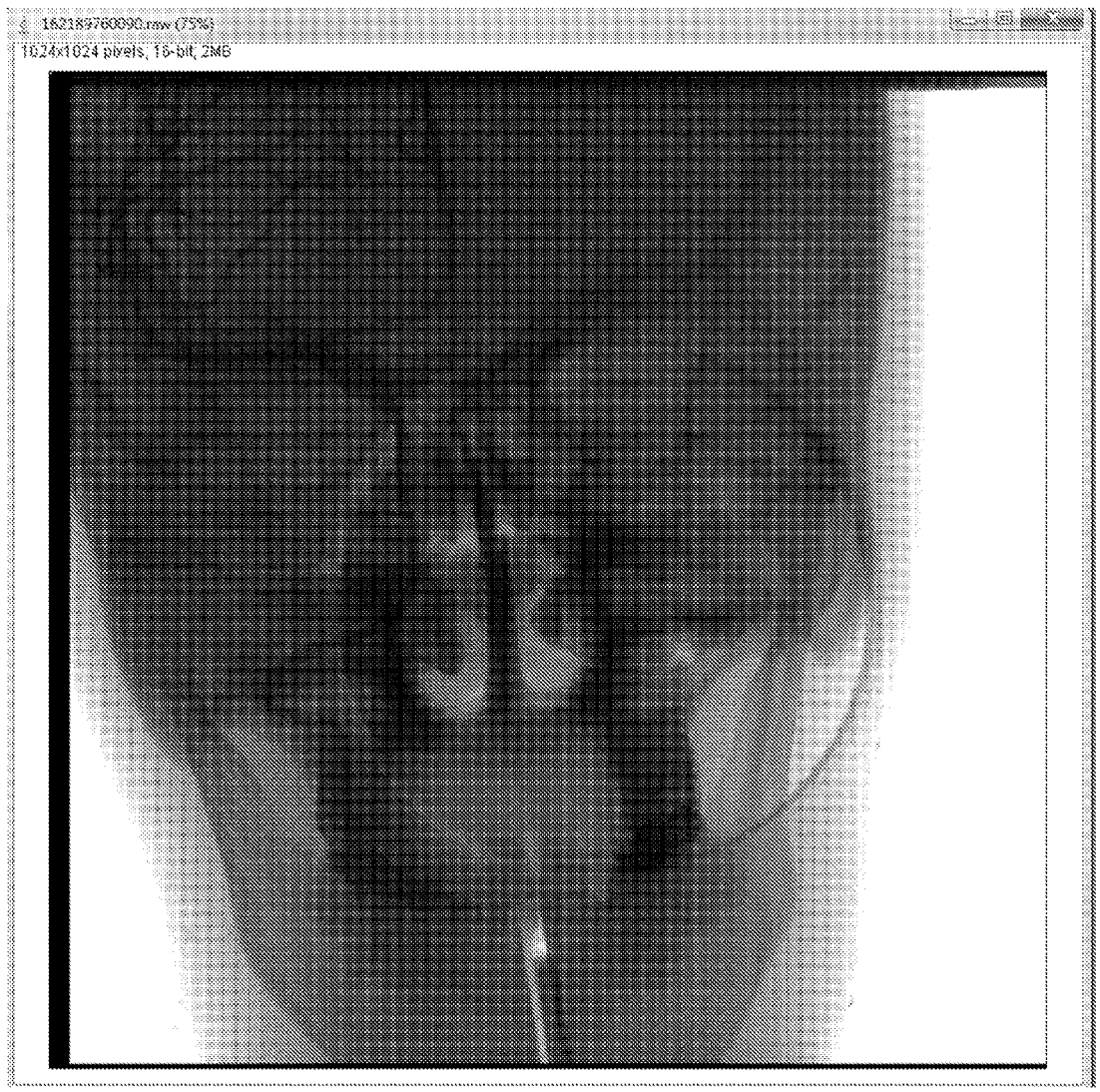
FIG. 19 is an image displayed according to the invention in which the image data sets corresponding to FIG. 17 have been acted upon by a TRF having a weight of 0.8 outside the ROI and a TRF having a weight of 0.2 inside the ROI. Note the reduction in noise in the ROI compared to FIG. 18.

A computer simulation has been performed and is described in the following paragraphs. The images from the sequence of an actual procedure that are shown in FIGS. 1-3 were reduced in brightness and mixed with Poisson noise to simulate the images obtained from ROI fluoroscopy (FIGS. 11 and 12). These images were played back at 20 fps and were sent to the GPU for real time processing. The images were first equalized to restore the image brightness (FIG. 13) and then the temporal filtering technique described above, using equation (1) was applied to the restored images (FIG. 14). From FIG. 13 it can be seen that the image outside the ROI is noisy due to fewer quanta incident on the receiver. Hence applying temporal filtering to this part of the image can reduce the noise and make it appear smoother.

The ability to perform an intervention (such as an EIGI) may be accomplished using the invention without materially denigrating the ability of the physician to perform the intervention. A larger temporal weight can be applied to that portion of the image data representing the area outside the ROI because movement in the periphery region would not be as crucial to the intervention since the image of the periphery region is used for monitoring whether anything should go radically wrong during the intervention (FIG. 14). If needed a higher filter weight inside the ROI also can be applied, however at the cost of losing some temporal resolution.

In this document we describe how a multiple temporal recursive filter implemented on a GPU can help in providing improved image guidance during neurovascular interventions at realistically fast frame rates. We have also described its potential use in ROI fluoroscopy where patient dose can be lowered substantially in the periphery. These techniques can be used in clinical applications to achieve dose savings as well as improved image quality due to reduced scatter from the periphery entering the ROI image. Applications of the invention outside the medical field, for example in the industrial non-destructive testing field, also can be achieved in much the same way as described herein. In those instances, the "patient" may be an article of manufacture, such as a machine or machine part.

The use of different temporal weights to different parts of an image data set (with or without an attenuator), can be implemented to achieve improvements to existing fluoroscopy methods and systems, as well as to enable dose reduction for patients. The invention may allow for modulation of an x-ray beam entering the patient so that more x-ray photons enter the ROI, where they are most needed, and so that fewer x-ray photons enter the periphery regions. A result is that the patient dose can be reduced in the periphery regions (outside of the ROI), which may be needed for less critical purposes, such as for general orientation or monitoring.

Figure 20:
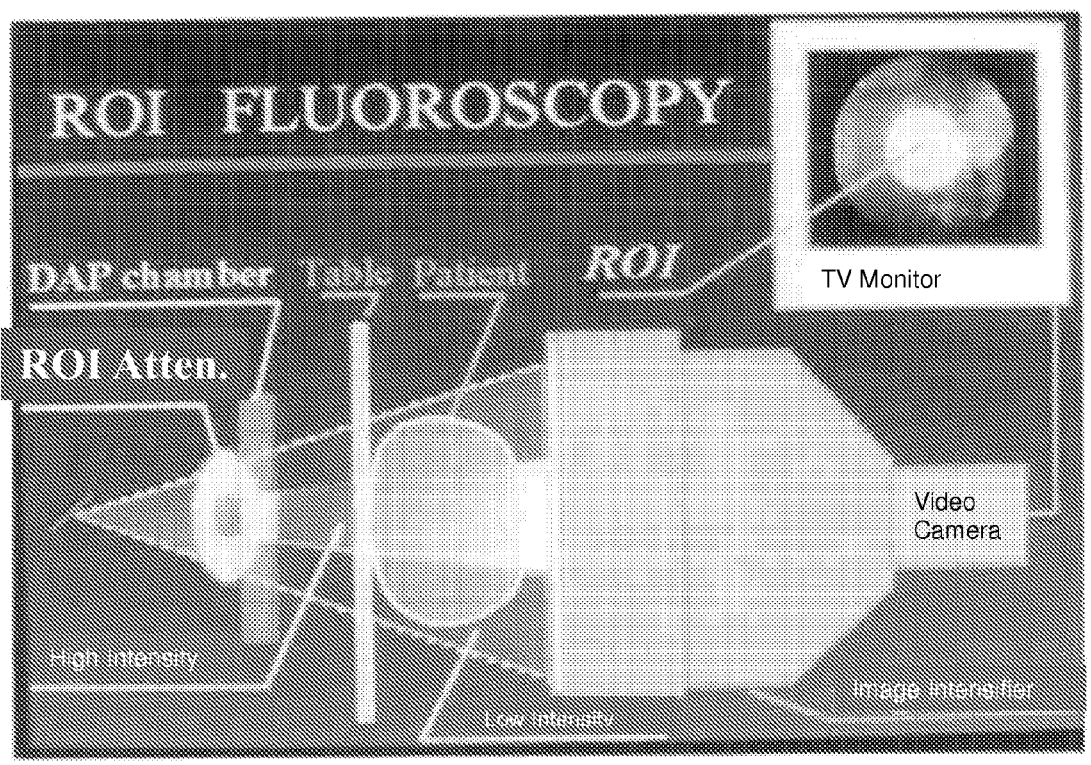
FIG. 20 is a schematic depicting basic principles of ROI imaging. When an attenuator is used, a lower intensity of radiation in the periphery (outside the ROI) reaches the patient, as well as the image intensifier. As such, it is possible to increase the overall intensity of the radiation emitted and thereby increase the radiation in the ROI in order to improve the image in the ROI, without increasing the overall radiation that reaches the patient. The ROI is chosen to be larger than the automatic-brightness-control (ABC) sensing region of the fluoroscopic unit in order to reduce interference with ABC operation. A dose-area-product (DAP) ionization chamber can be used to monitor patient radiation exposure.
Figure 21:
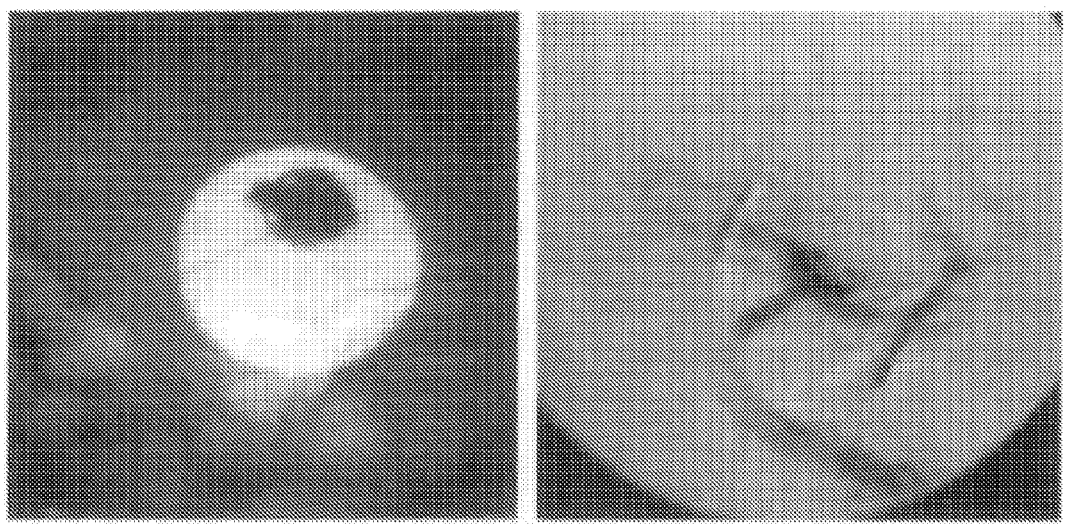
FIG. 21 is a fluoroscopically generated image of a subarachnoid hemorrhage from a basilar artery aneurysm in a 58 year-old man. In this neurointerventional study, the attenuator was four layers of Lanex screens (0.27 g/cm$^2$ gadolinium) (10% filter transmission) and the ROI was 14% of the field of view ("FOV").

In previous techniques, an attenuator (perhaps metallic or other x-ray absorbent material) was placed between the x-ray source and the patient to reduce the intensity of the x-ray beam. For example, a flat piece of metal with a central hole, such as that which is illustrated in FIG. 20, could be used as an attenuator. The patient dose outside the ROI would thus be substantially reduced depending upon the energy of the x-rays and the attenuation properties of the attenuator. If no manipulation of the image data occurred, the resulting image would appear dark in the periphery because of the reduced x-ray fluence due to attenuation caused by the attenuator. However, the displayed image could be equalized by subtracting a mask image. Such a mask image could be generated by using a uniform phantom that was taken prior to the patient study, or if angiography were desired, then merely by using the mask normally acquired during digital subtraction angiography (DSA). For clarity, in DSA, the attenuator would be treated just as other background, such as bone and soft tissue, by being subtracted from the final angiogram (see FIG. 21). FIG. 20 shows a system in which an image intensifier was used as the receiver. Other systems might utilize a flat panel receiver.

The present invention may enable further improvements to fluoroscopy systems. In particular, the invention may be used to enable (1) a moveable ROI using a single "roadmap", (2) a movable ROI using software to move the ROI within an FOV, (3) automatic ROI position tracking with a selected interventional feature of interest, or (4) a combination of a higher-exposure ROI with a higher-resolution detector ROI. Each of these four additional improvements are described further in the following paragraphs.

Figure 22:
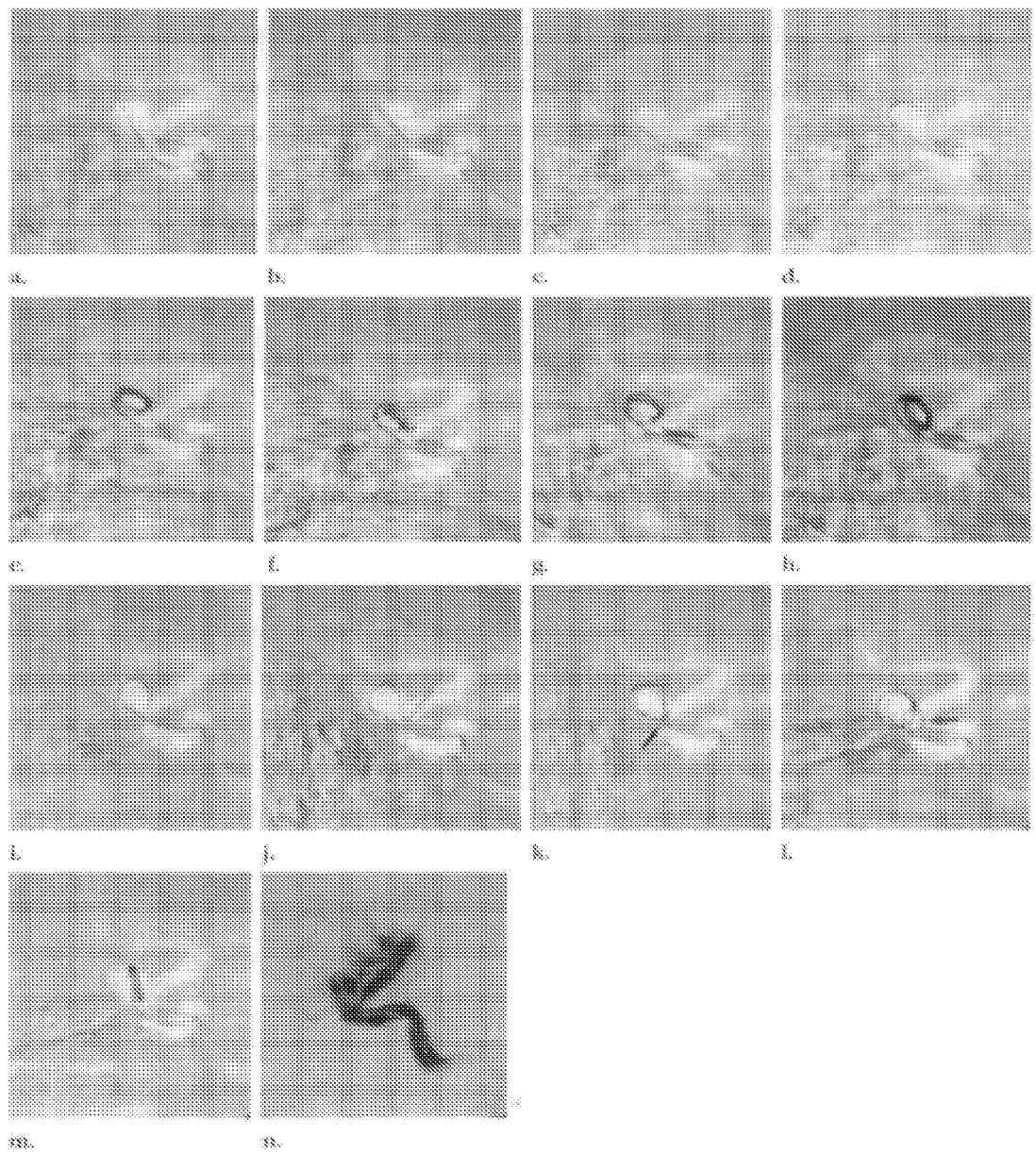
FIG. 22 is a sequence images (left internal carotid artery injection, oblique view) demonstrating the use of mapping in a 48 year-old woman with a left carotid-opthalmic artery aneurysm. In this neurointerventional study, the attenuator thickness was two layers (0.135 g/cm$^2$ gadolinium) (30% filter transmission) and the ROI was 14% of the FOV.

"Roadmapping" is the method used to create a map of the patient's vascular system. The map can then be used to guide a wire to a site within the patient for the purpose of effecting a treatment. As the wire is fed into the patient, the ROI may be moved in order to track the location of the tip of the wire. In the prior art, moving the ROI often necessitated re-injecting the patient in order to acquire a new roadmap corresponding to the new ROI. Roadmapping was used in the fixed ROI procedure corresponding to the images of FIG. 22.

For a fixed ROI placed centrally in an FOV, movement of the patient or the gantry to try to place the ROI over a changed location, perhaps where the interventional site has moved, would displace the roadmap causing it to be invalid and forcing a new patient contrast media injection to be done to form a new roadmap corresponding to the new position. In lieu of moving the patient or the gantry, we propose that the gantry and patient stay fixed, and instead allow the ROI to move. For example, in a situation where an attenuator is being used, the attenuator may be moved (perhaps using precise motors) so as to maintain the position of the higher exposure region over the changing region of clinical interest within the FOV, even if this ROI is moved off-center with regard to the FOV, which may occur as the intervention proceeds. High-speed image processing computers would then maintain and utilize the same roadmap, but enable a new virtual mask to be used to equalize the field regardless of the location of the ROI in the FOV.

A second improvement that may be implemented using the invention involves identifying those pixels that are within the ROI (or outside the ROI). When the ROI location has moved (e.g. the wire tip has moved), the list of pixels identified as being in the ROI (or outside the ROI) is changed to match the new location of the ROI. For example, when the user desires to alter the location of the ROI, the new location for the ROI is identified, and pixels corresponding to the new ROI location are then associated with the temporal filter for the ROI, and the displayed image then changes to reflect the new ROI location.

It should be noted that one type of temporal filter may be used for the ROI and another temporal filter may be used for the periphery region in order to achieve a desired quality for the displayed image. Or the same type of temporal filter can be used in both regions, but with different weights, and in this manner, the increased quantum noise in the periphery region due to the reduced photon fluence could be "compensated" or the apparent noise reduced by increasing the recursive software filtering, while doing less or no temporal averaging within the ROI itself so that there is minimal temporal lag within the ROI of the displayed image.

A third improvement is to use feature recognition software to track a selected interventional feature of interest such as a catheter tip as it is moved through the full FOV and to automatically move the region of interest of higher exposure such that the feature remains centered in the perhaps off-centered ROI.

A fourth improvement involves using the moveable higher exposure ROI in conjunction with an image receptor with positionally controllable spatial resolution so that a higher exposure region coincides with a region of higher resolution, both of which could move over the full FOV as the interventional feature of interest is moved, providing both improved resolution and signal to noise ratio. Such an image receptor could be realized using a tiling of detector modules and differential binning of pixels between modules or some other implementation using large FOV flat panel detectors.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of displaying an image corresponding to a dynamic x-ray of an object, comprising:
   providing an object to be imaged, the object having a first part and a second part, wherein the object is provided relative to an attenuator so that the attenuator resides between an x-ray source and the object so as to provide more attenuation of x-rays traveling toward the second part than for x-rays traveling toward the first part;
   gathering a first image data set ("IDS") that is representative of an x-ray of the object at a first time;
   identifying a first portion of the first IDS and a second portion of the first IDS, wherein the first portion of the first IDS is representative of the first part of the object, and the second portion of the first IDS is representative of the second part of the object;
   gathering a second IDS that is representative of an x-ray of the object at a second time;
   identifying a first portion of the second IDS and a second portion of the second IDS, wherein the first portion of the second IDS is representative of the first part of the object, and the second portion of the second IDS is representative of the second part of the object;
   applying a first temporal filter to combine the first portion of the first IDS and the first portion of the second IDS, in order to produce a first display data set that is representative of the first part of the object;
   applying a second temporal filter to combine the second portion of the first IDS and the second portion of the second IDS, in order to produce a second display data set that is representative of the second part of the object;
   displaying an image of the object, wherein a first part of the image depicting the first part of the object represents the first display data set, and a second part of the image depicting the second part of the object represents the second display data set so that the first part of the image and the second part of the image result from the application of different filters.

2. The method of claim 1, wherein the first IDS includes pixel data, each pixel data representing radiation received at a specific pixel location on a receiver.

3. The method of claim 1, wherein the first IDS is gathered using a fluoroscopic x-ray system.

4. The method of claim 1, wherein the second IDS is gathered using a fluoroscopic x-ray system.

5. The method of claim 1, wherein the first portion of the first IDS and the first portion of the second IDS are selected to include a catheter tip.

6. The method of claim 1, wherein the first portion of the first IDS and the second IDS is selected to include a treatment site.

7. The method of claim 1, wherein the first filter is a temporal filter that:
   multiplies data of the first IDS by a number $\alpha$ to produce a first output;
   multiplies data of the second IDS by a number $\beta$ to produce a second output; and
   adds the first output to the second output to produce the first display data set.

8. The method of claim 7, wherein the data of the first IDS include a plurality of pixel data, and each pixel data represents radiation received at a specific pixel location.

9. The method of claim 7, wherein the first filter adds the first and second outputs by adding data of the first output that corresponds to data of the second output, wherein data of the first output that corresponds to data of the second output are derived from the same pixel location.

10. The method of claim 7, wherein the second filter is a temporal filter that:
    multiplies data of the first IDS by a number $\psi$, where $\psi$ is different from $\alpha$; to produce a third output;
    multiplies data of the second IDS by a number $\omega$ to produce a fourth output; and
    adds the third output to the fourth output to produce the second display data set.

11. The method of claim 1, wherein the first filter is a recursive filter that:
    derives a first output using data of the first IDS;
    multiplies the first output by a number $\alpha$;
    multiplies data of the second IDS by a number $\beta$, where $\beta$ equals $1-\alpha$, to produce a second output; and
    adds the first output to the second output to produce the first display data set.

12. The method of claim 11, wherein the data of the first IDS include a plurality of pixel data, and each pixel data represents radiation received at a specific pixel location.

13. The method of claim 11, wherein the first filter adds the first and second outputs by adding data of the first output that corresponds to data of the second output, wherein data of the first output that corresponds to data of the second output are derived from the same pixel location.

14. The method of claim 11, wherein the second filter is a recursive filter that:
    derives a third output using data of the first IDS;
    multiplies the third output by a number $\psi$, where $\psi$ is different from $\alpha$;
    multiplies data of the second IDS by a number $\omega$, where $\omega$ equals $1-\psi$, to produce a fourth output and
    adds the third output to the fourth output to produce the second display data set.

15. The method of claim 1, wherein the first display data set is produced from a weighted sum of the first portion of the second IDS and a prior first display data set.

16. The method of claim 15, wherein the second display data set is produced from a weighted sum of the second portion of the second IDS and a prior second display data set.

17. A system for displaying an image corresponding to a dynamic x-ray, comprising:
   (a) a monitor that is able to display an image; and
   (b) a microprocessor programmed to:
      gather a first image data set ("IDS") that is representative of an x-ray of an object at a first time;
      identify a first portion of the first IDS and a second portion of the first IDS, wherein the first portion of the first IDS is representative of a first part of the object, and the second portion of the first IDS is representative of a second part of the object;
      gather a second IDS that is representative of an x-ray of the object at a second time;
      identify a first portion of the second IDS and a second portion of the second IDS, wherein the first portion of the second IDS is representative of the first part of the object, and the second portion of the second IDS is representative of the second part of the object;
      apply a first temporal filter to combine the first portion of the first IDS and the first portion of the second IDS, in order to produce a first display data set that is representative of the first part of the object;
      apply a second temporal filter to combine the second portion of the first IDS and the second portion of the second IDS, in order to produce a second display data set that is representative of the second part of the object;
      display via the monitor an image of the object, wherein a first part of the image depicting the first part of the object represents the first display data set, and a second part of the image depicting the second part of the object represents the second display data set so that the first part of the image and the second part of the image result from the application of different filters; and
   (c) an attenuator residing between an x-ray source and the object, the attenuator providing more attenuation of x-rays traveling toward the second part than for x-rays traveling toward the first part.

18. The system of claim 17, wherein the first IDS includes a plurality of pixel data, and each pixel data represents radiation received at a specific pixel location on a receiver.

19. The system of claim 17, wherein the first IDS is gathered using a fluoroscopic x-ray system.

20. The system of claim 17, wherein the second IDS is gathered using a fluoroscopic x-ray system.

21. The system of claim 17, wherein the first filter is a temporal filter that:
   multiplies data of the first IDS by a number a, to produce a first output;
   multiplies data of the second IDS by a number β, to produce a second output ; and
   adds the first output to the second output to produce the first display data set.

22. The system of claim 21, wherein the data of the first IDS include a plurality of pixel data, and each pixel data represents radiation received at a specific pixel location.

23. The system of claim 21, wherein the first filter adds the first and second outputs by adding data of the first output that corresponds to data of the second output, wherein data of the first output that corresponds to data of the second output are derived from the same pixel location.

24. The system of claim 21, wherein the second filter is a temporal filter that:
   multiplies data of the first IDS by a number ψ, where ψ is different from α, to produce a third output;
   multiplies data of the second IDS by a number ω, to produce a fourth output; and
   adds the third output to the fourth output to produce the second display data set.

25. The system of claim 17, wherein the first filter is a recursive filter that:
   derives a first output using data of the first IDS;
   multiplies the first output by a number α;
   multiplies data of the second IDS by a number β, where β equals 1-α, to produce a second output; and
   adds the first output to the second output to produce the first display data set.

26. The system of claim 25, wherein the data of the first IDS include a plurality of pixel data, each pixel data represents radiation received at a specific pixel location.

27. The system of claim 25, wherein the data of the first IDS that corresponds to the data of the second IDS have the same pixel location.

28. The system of claim 25, wherein the second filter is a recursive filter that:
   derives a third output using data of the first IDS;
   multiplies the third output by a number ψ, where ψ is different from α;
   multiplies data of the second IDS by a number ω, where ω equals 1-ψ, to produce a fourth output; and
   adds the third output to the fourth output to produce the second display data set.

29. The system of claim 17, wherein the microprocessor is programmed to produce the first display data set from a weighted sum of the first portion of the second IDS and a prior first display data set.

30. The system of claim 29, wherein the microprocessor is programmed to produce the second display data set from a weighted sum of the second portion of the second IDS and a prior second display data set.

* * * * *